(12) United States Patent
Faehsing

(10) Patent No.: US 12,011,207 B2
(45) Date of Patent: Jun. 18, 2024

(54) METHOD FOR OPERATING AN ELECTROSURGICAL SYSTEM AND ULTRASOUND GENERATOR

(71) Applicant: OLYMPUS WINTER & IBE GMBH, Hamburg (DE)

(72) Inventor: Thomas Faehsing, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 831 days.

(21) Appl. No.: 17/259,433

(22) PCT Filed: Jul. 2, 2019

(86) PCT No.: PCT/EP2019/067680
§ 371 (c)(1),
(2) Date: Jan. 11, 2021

(87) PCT Pub. No.: WO2020/011594
PCT Pub. Date: Jan. 16, 2020

(65) Prior Publication Data
US 2021/0275242 A1 Sep. 9, 2021

(30) Foreign Application Priority Data
Jul. 11, 2018 (DE) ..................... 10 2018 116 771.7

(51) Int. Cl.
*A61B 17/32* (2006.01)
*A61B 18/12* (2006.01)
(Continued)

(52) U.S. Cl.
CPC ...... *A61B 18/12* (2013.01); *A61B 17/320092* (2013.01); *B06B 1/0207* (2013.01);
(Continued)

(58) Field of Classification Search
CPC .... A61B 17/320092; A61B 2017/0003; A61B 2017/00106; A61B 2017/00194; A61B 2017/320094; A61B 2017/00994
See application file for complete search history.

(56) References Cited

U.S. PATENT DOCUMENTS 6,678,621 B2 * 1/2004 Wiener .......... A61B 17/320068
606/178
6,761,690 B2 * 7/2004 Sakurai ................. B06B 1/0253
600/443
(Continued)

FOREIGN PATENT DOCUMENTS

DE  10 2012 109 037 A1  4/2014
DE  10 2015 204 127 A1  9/2016
(Continued)

OTHER PUBLICATIONS

Jan. 3, 2023 Intention to Grant Patent issued in European Patent Application No. 19737689.0.
(Continued)

*Primary Examiner* — Ryan J. Severson
(74) *Attorney, Agent, or Firm* — Oliff PLC

(57) ABSTRACT

A method for operating an electrosurgical system including an ultrasound generator and an ultrasonic instrument, includes the steps: determining an initial resonant frequency of the ultrasonic instrument by the ultrasound generator, energizing the ultrasonic instrument by the ultrasound generator with an operating amplitude and an operating frequency which correspond to the initial resonant frequency, tracking the operating frequency of the ultrasound generator with changes in the resonant frequency of the ultrasonic instrument, and terminating the energizing of the ultrasonic instrument by the ultrasound generator. A method terminates the energizing of the ultrasonic instrument by the ultrasound generator, in a decay phase the operating amplitude of the (Continued)

Figure 1:
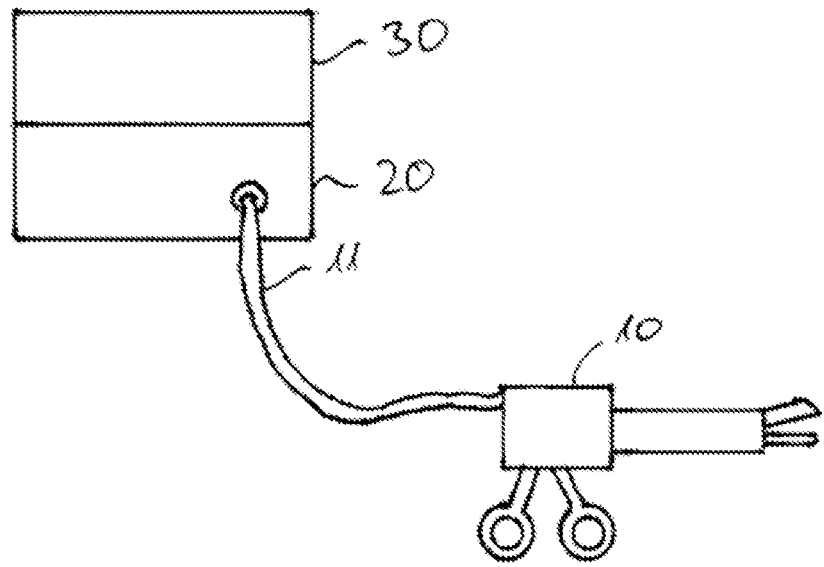

ultrasound generator is reduced to zero with a predefined or predefinable rate of change. An ultrasound generator is also presented.

8 Claims, 3 Drawing Sheets

(51) Int. Cl.
  *B06B 1/02* (2006.01)
  *A61B 17/00* (2006.01)
  *A61B 18/00* (2006.01)
(52) U.S. Cl.
  CPC .............. *A61B 2017/0003* (2013.01); *A61B 2017/00106* (2013.01); *A61B 2017/00194* (2013.01); *A61B 2018/0075* (2013.01); *A61B 2018/00994* (2013.01); *B06B 2201/40* (2013.01)

(56) References Cited

U.S. PATENT DOCUMENTS

| | | | | |
|---|---|---|---|---|
| 7,077,853 B2* | 7/2006 | Kramer | ......... | A61B 17/320068 702/75 |
| 7,393,356 B2* | 7/2008 | Tanaka | ......... | A61B 17/320068 606/169 |
| 8,845,537 B2* | 9/2014 | Tanaka | ......... | A61B 18/148 600/439 |
| 8,858,439 B2* | 10/2014 | Tanaka | ......... | A61B 17/320092 600/439 |
| 10,588,685 B2* | 3/2020 | Assmus | ......... | A61B 18/1206 |
| 10,912,580 B2* | 2/2021 | Green | ......... | A61B 18/1206 |
| 11,129,669 B2* | 9/2021 | Stulen | ......... | A61B 18/1445 |
| 2002/0062132 A1* | 5/2002 | Kramer | ......... | A61B 17/320068 606/169 |
| 2002/0165680 A1* | 11/2002 | Wiener | ......... | A61B 17/320068 702/75 |
| 2003/0199793 A1* | 10/2003 | Sakurai | ......... | B06B 1/0253 601/2 |
| 2004/0102709 A1* | 5/2004 | Tanaka | ......... | A61B 17/320068 600/459 |
| 2010/0312107 A1* | 12/2010 | Tanaka | ......... | A61B 18/148 600/439 |
| 2010/0312111 A1* | 12/2010 | Tanaka | ......... | A61B 17/320092 600/443 |
| 2013/0310689 A1* | 11/2013 | Nishigaki | ......... | B06B 1/0215 600/437 |
| 2016/0324537 A1* | 11/2016 | Green | ......... | A61B 18/1206 |
| 2017/0000516 A1* | 1/2017 | Stulen | ......... | A61B 18/1445 |
| 2018/0042660 A1* | 2/2018 | Assmus | ......... | A61B 18/1206 |
| 2021/0228259 A1* | 7/2021 | Faehsing | ......... | A61B 17/320092 |
| 2021/0275242 A1* | 9/2021 | Faehsing | ......... | B06B 3/00 |
| 2022/0039891 A1* | 2/2022 | Stulen | ......... | A61B 18/12 |

FOREIGN PATENT DOCUMENTS

| | | |
|---|---|---|
| EP | 1 199 048 A2 | 4/2002 |
| EP | 1199047 A2 | 4/2002 |
| EP | 1 835 622 A2 | 9/2007 |
| WO | 2013/154925 A2 | 10/2013 |
| WO | 2016/091401 A1 | 6/2016 |

OTHER PUBLICATIONS

Jun. 17, 2019 Office Action issued in German Patent Application No. 10 2018 116 771.7.
Sep. 23, 2019 Search Report and Written Opinion issued in International Patent Application No. PCT/EP2019/067680.
Jan. 12, 2021 International Preliminary Report on Patentability issued in International Patent Application No. PCT/EP2019/067680.

\* cited by examiner

METHOD FOR OPERATING AN ELECTROSURGICAL SYSTEM AND ULTRASOUND GENERATOR

The invention relates to a method for operating an electrosurgical system comprising an ultrasound generator and an ultrasonic instrument, comprising the steps: determining an initial resonant frequency of the ultrasonic instrument by means of the ultrasound generator, energizing the ultrasonic instrument by means of the ultrasound generator with an operating amplitude and an operating frequency which correspond to the initial resonant frequency, tracking the operating frequency of the ultrasound generator with changes in the resonant frequency of the ultrasonic instrument, and terminating the energizing of the ultrasonic instrument by the ultrasound generator.

The invention also relates to an ultrasound generator.

In modern electrosurgery, in addition to pure electrosurgical procedures, in which a surgical effect is achieved exclusively through electrical currents, procedures and instruments are also used in which a high-frequency electrical signal is converted into an ultrasound oscillation by means of an ultrasound transducer, which then causes a surgical effect. A surgical effect caused by the flow of current and a surgical effect caused by ultrasound can be combined.

Corresponding electrosurgical systems have an ultrasound generator for this purpose. This ultrasound generator generates a high-frequency electrical signal with which the ultrasonic instrument is energized. The ultrasonic instrument comprises an ultrasound transducer, which is usually a piezoelectrical element that generates an ultrasound oscillation when the high-frequency electrical signal is applied. The ultrasound oscillation is transmitted to a working element in the ultrasonic instrument that causes a surgical effect when it comes into contact with biological tissue. The working element is also referred to as a sonotrode.

In order to achieve an effective surgical effect, the ultrasound transducer is operated at its resonant frequency. This resonant frequency depends on the one hand on the type of ultrasonic instrument, but on the other hand also on manufacturing tolerances of the components of the ultrasonic instrument and on external factors such as, e.g., the mechanical load during use of the ultrasonic instrument. The resonant frequency is usually between 10 kHz and 100 kHz, for example 50 kHz.

In order to be able to energize the ultrasound transducer in its resonant frequency, the ultrasound generator is configured to determine this resonant frequency. For this purpose, the ultrasound generator carries out a so-called scan process when the ultrasonic instrument is not under load, in which the ultrasound transducer is controlled with different frequencies. Since the strength of the mechanical ultrasound oscillation cannot be measured directly, the ultrasound generator constantly measures the current and voltage of the high-frequency electrical signal and determines the phase position between the two variables. The phase position can be used to determine whether the frequency of the high-frequency electrical signal corresponds to the resonant frequency of the ultrasound transducer. At the resonant frequency, the current and voltage of the high-frequency signal are in phase. Spurious resonances, in which the current and voltage are also in phase, can be excluded by means of suitable additional conditions.

During use, the resonant frequency changes, for example, due to changing mechanical loads on the ultrasonic instrument or temperature changes. To track the operating frequency of the high-frequency electrical signal when the resonant frequency changes, the ultrasound generator continues to measure the phase position of the current and voltage and controls the operating frequency such that the current and voltage remain in phase.

When an electrosurgical procedure or a partial step of an electrosurgical procedure has been completed, the energizing of the ultrasonic instrument by the ultrasound generator is terminated. For this purpose, the high-frequency electrical signal is usually deactivated.

In this case, however, the problem arises that electrical energy and mechanical energy are stored in the system comprising the ultrasound generator and the ultrasonic instrument. Without the frequency-determining high-frequency electrical signal, this energy can stimulate natural oscillations of the system at other frequencies that are not matched to the ultrasound transducer. This can lead to current and/or voltage peaks that can damage or even destroy the ultrasonic instrument.

It is therefore the object of the invention to provide a method for operating an electrosurgical system and an ultrasound generator that are improved with regard to the problem described.

According to one aspect of the invention, the object is achieved by a method for operating an electrosurgical system comprising an ultrasound generator and an ultrasonic instrument, comprising the steps: determining an initial resonant frequency of the ultrasonic instrument by means of the ultrasound generator, energizing the ultrasonic instrument by means of the ultrasound generator with an operating amplitude and an operating frequency which correspond to the initial resonant frequency, tracking the operating frequency of the ultrasound generator with changes in the resonant frequency of the ultrasonic instrument, and terminating the energizing of the ultrasonic instrument by the ultrasound generator, which is further developed in that, to terminate the energizing of the ultrasonic instrument by the ultrasound generator, in a decay phase the operating amplitude of the ultrasound generator is reduced to zero with a predefined or predefinable rate of change.

The method according to the invention ensures that the oscillation frequency of the system consisting of the ultrasound generator and the ultrasonic instrument is predefined by the operating frequency of the ultrasound generator during the termination of the energizing, and thus excitation of other natural oscillations cannot occur. The energy stored in the system is broken down through ohmic losses and mechanical friction without current or voltage peaks occurring.

The termination of the energizing of the ultrasonic instrument is often accompanied by the removal of the ultrasonic instrument from the tissue to be treated. This can change the mechanical load on the ultrasonic instrument and thus also the resonant frequency of the ultrasound transducer in a short time In a preferred embodiment of a method according to the invention, the operating frequency of the ultrasound generator can therefore be tracked with changes in the resonant frequency of the ultrasonic instrument at least in a first portion of the decay phase. This ensures that the operating frequency corresponds to the resonant frequency even if the resonant frequency of the ultrasound transducer changes during the decay phase.

To be able to track the operating frequency of the ultrasound generator with the resonant frequency of the ultrasound transducer, however, a reliable determination of the phase position between the current and the voltage of the high-frequency electrical signal is required, for which a sufficient operating amplitude of the ultrasound generator is required. If the operating amplitude falls below this value, phase determination and frequency tracking are no longer possible.

In a further preferred embodiment of the invention, the operating frequency of the ultrasound generator can therefore be kept at a constant value at least in a second portion of the decay phase. Thus, even with a low operating amplitude of the ultrasound generator, uncontrolled oscillating behavior of the system can be prevented.

The transition between the first portion and the second portion of the decay phase can take place particularly preferably when the operating amplitude of the ultrasound generator falls below a predefined or predefinable limit value.

In an alternative embodiment of the invention, the transition between the first portion and the second portion of the decay phase can take place at a predefined or predefinable time after the initiation of the decay phase.

The operating frequency of the ultrasound generator can be kept in the second portion of the decay phase at a value that corresponds to a mean value of the operating frequency of the ultrasound generator in a predefined or predefinable time portion before the start of the second portion of the decay phase. In this case, the probability is particularly high that the operating frequency corresponds particularly well to the actual resonant frequency. Either an arithmetic mean value, or a sliding mean value, a median value, or a modal value can be used as the mean value in the context of the invention.

The predefined or predefinable time portion can preferably be completely before the start of the decay phase.

According to a further aspect of the invention, the object is achieved by an ultrasound generator of an electrosurgical system comprising an ultrasound generator and an ultrasonic instrument, the ultrasound generator being configured to operate the electrosurgical system according to a method according to the above statements. With regard to the effects and advantages achieved in this way, express reference is made to what has been said above.

In the following, the invention shall be explained in more detail using some exemplary representations. The illustrated exemplary embodiments serve only to provide a better understanding of the invention without restricting it.

Shown in the drawings are:
FIG. 1: an electrosurgical system,
FIG. 2: the structure of an ultrasonic instrument,
FIG. 3: the phase response of an ultrasound transducer,
FIG. 4: the schematic structure of an ultrasound generator,
FIG. 5: the operating frequency and operating amplitude of the ultrasound generator in the decay phase.

FIG. 1 shows an electrosurgical system having an ultrasonic instrument 10, an ultrasound generator 20, and a high-frequency generator 30. The ultrasonic instrument 10 is connected to the ultrasound generator 20 via a cable 11.

The ultrasonic instrument 10 can, for example, be a combined high-frequency and ultrasound forceps, such as those sold by Olympus Corporation under the name THUNDERBEAT.

During operation, the ultrasound generator 20 generates a first high-frequency electrical signal that is transmitted via the cable 11 to the ultrasonic instrument 10, and there is converted into an ultrasound oscillation by an ultrasound transducer (not shown). The ultrasound oscillation is coupled into a sonotrode, not shown, which can be brought into direct or indirect contact with tissue to be treated.

The high-frequency generator 30 generates a second high-frequency electrical signal during operation, which is transmitted via an internal connection to the ultrasound generator 20 and from there, also via the cable 11, to the ultrasonic instrument 10. In the ultrasonic instrument 10, the second high-frequency electrical signal is fed to one or more electrodes, which can be brought into direct or indirect contact with the tissue to be treated.

Figure 2:
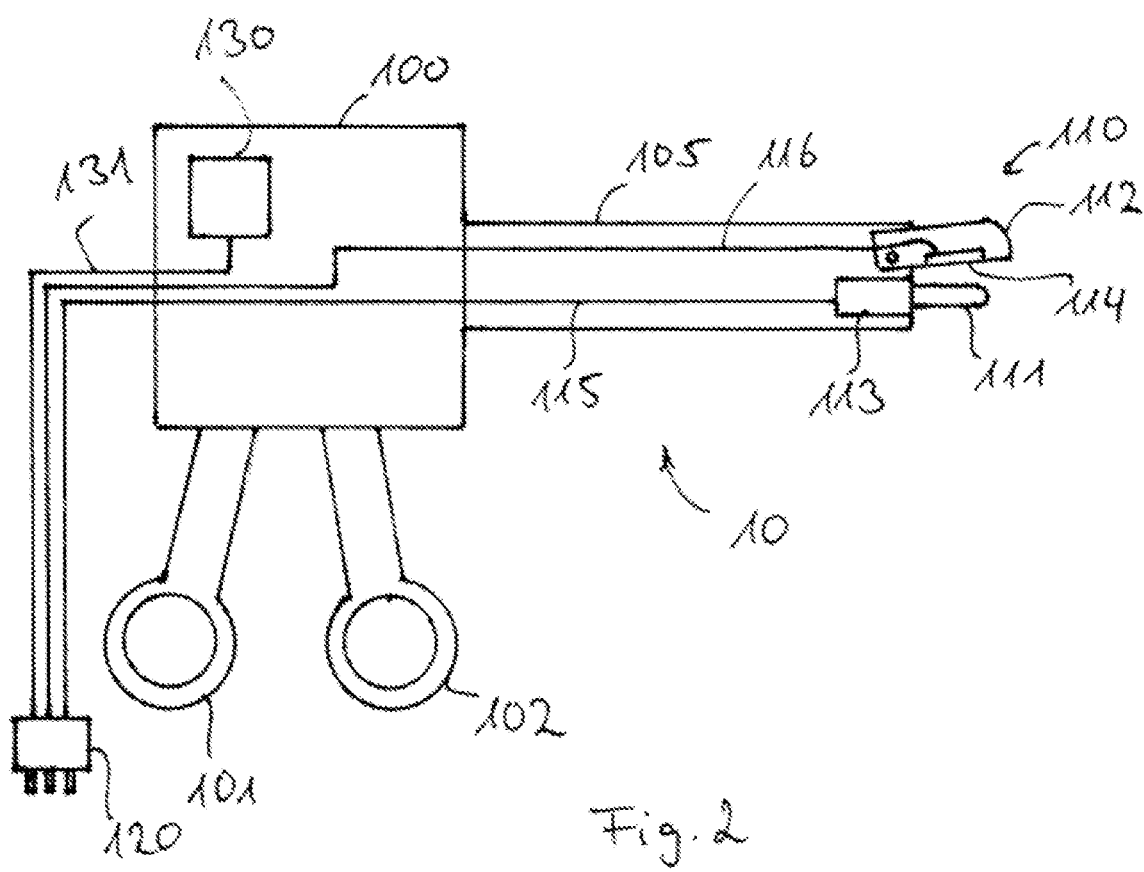

In FIG. 2, the structure of the ultrasonic instrument 10 is shown in more detail, wherein the illustration is not true to scale and is greatly simplified.

The ultrasonic instrument 10 consists of a main body 100 with handle levers 101, 102. A shaft 105 adjoins the main body 100, at the distal end of which a forceps mouth 110 is arranged.

The forceps mouth 110 here comprises a fixed branch, which is formed by a sonotrode 111, and a movable branch 112. The sonotrode 111 is coupled to an ultrasound transducer 113. An electrode 114 is arranged on the movable branch 112.

The movable branch 112 can be moved in the direction of the sonotrode 111 by actuating one of the handle levers 101, 102, so that the forceps mouth 110 closes. A portion of human or animal tissue, not shown, which is clamped in the closed forceps mouth 110, can then be treated by activating the sonotrode 111 and/or the electrode 114.

To activate the sonotrode 111, a first high-frequency electrical signal is fed from the ultrasound generator 20 to the ultrasound transducer 113. This converts the signal into an ultrasound oscillation and transmits this to the sonotrode 111. The mechanical movement of the sonotrode 111, which is in close contact with the tissue to be treated, then causes a surgical effect in the tissue, which can vary depending on the design of the sonotrode and the desired result.

To activate the electrode 114, a second high-frequency electrical signal is fed to it from the electrosurgical generator 30.

The electrical signals are supplied via lines 115, 116. The lines 115, 116 end in a plug 120 that can be connected to the ultrasound generator 20.

The ultrasonic instrument 10 further comprises a memory element 130, the function of which will be explained later. The memory element 130 is also connected to the plug 120 via a line 131.

In order to achieve an optimal surgical effect, it is desirable that the ultrasound generator 20 energizes the ultrasound transducer 113 at its mechanical resonant frequency. This mechanical resonant frequency, however, depends on various parameters, for example manufacturing tolerances of the ultrasound transducer 113, but also on the type and quantity of the tissue gripped in the forceps mouth 110 and the contact pressure of the movable branch 112, as well as numerous other parameters such as the temperature of the ultrasound transducer and the degree of wear and/or contamination of the ultrasonic instrument. These and other influencing parameters are known to the person skilled in the art.

In order to determine the current resonant frequency of the ultrasound transducer 113 at the start of an activation phase, the ultrasound generator 20 carries out a so-called scan, wherein the ultrasound transducer is energized successively with several frequencies and the course of the phase position of the current and voltage of the first high-frequency electrical signal is measured.

Figure 3:
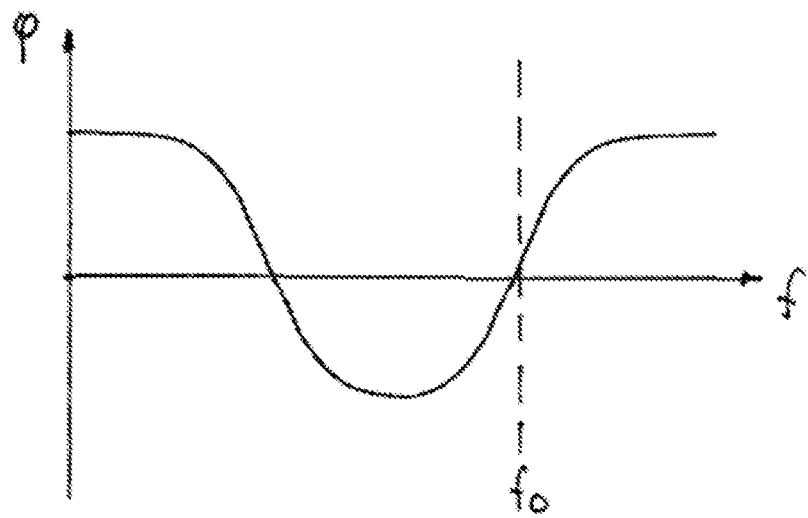

The course of the phase position $\varphi$ of current and voltage as a function of the operating frequency f is shown in FIG. 3. It can be seen that at a low operating frequency there is initially a positive phase position, that is, the current leads the voltage. As the operating frequency rises, the phase decreases, passes through the zero point, and initially becomes negative. In this frequency range, the voltage leads the current. When approaching the resonant frequency $f_0$, the phase φ rises again and passes through the zero point again when the resonant frequency $f_0$ is reached, in order to become positive as the operating frequencies continue to rise. Here again the current leads the voltage.

The phase progression at low operating frequencies is determined by a structure-related parallel capacitance. This mainly concerns the capacitive effect of contacting surfaces that are vapor-deposited on the piezo crystals of the ultrasound transducer.

Figure 4:
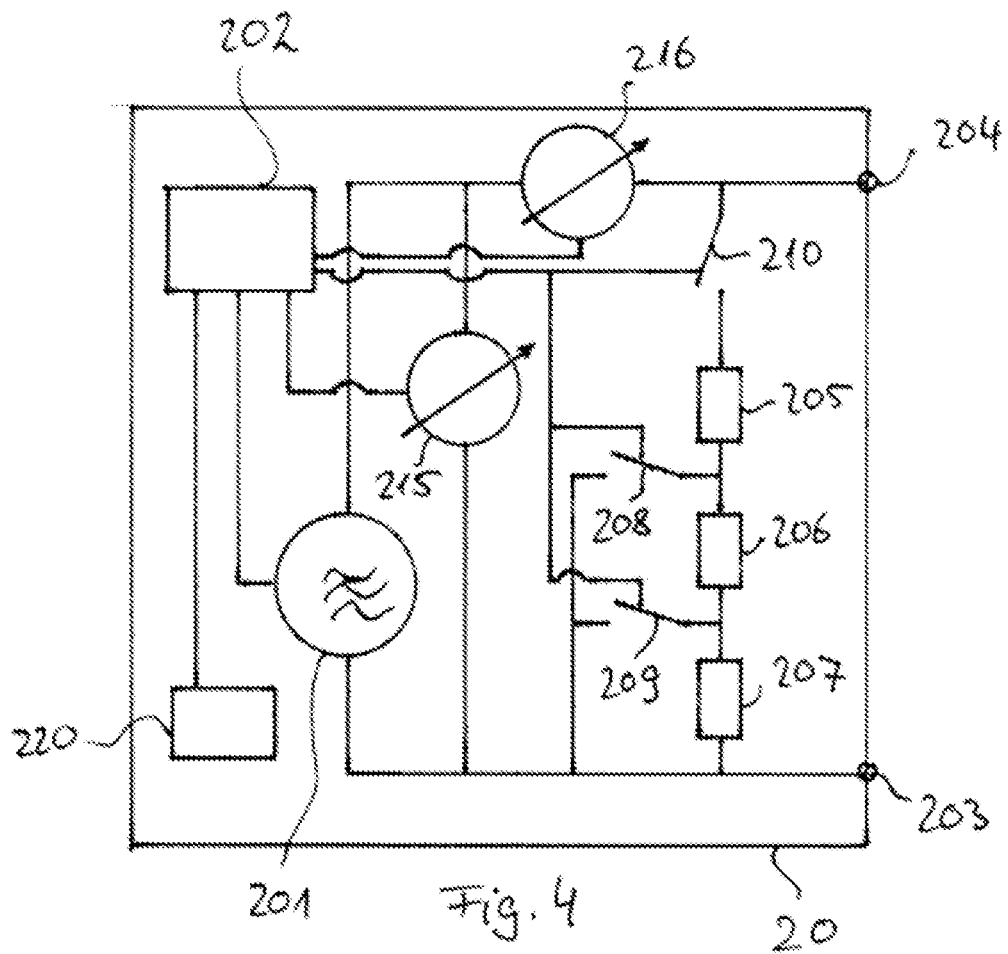

In FIG. 4, the structure of the ultrasound generator 20 is shown schematically insofar as it is relevant for understanding the invention.

An oscillator 201 generates a high-frequency electrical signal with a controllable frequency. The operating frequency of the oscillator 201 is controlled by a controller 202. The high-frequency electrical signal is provided at output terminals 203, 204, which can be connected to contacts of the plug 120 of the ultrasonic instrument 10.

Inductances 205, 206, 207 are arranged between the output terminals 203, 204, which inductances can be switched on or off by switches 208, 209, 210. The inductances 205, 206, 207 serve to compensate for the phase shift between the current and voltage of the high-frequency electrical signal, which is caused by the parallel capacitance of the ultrasound transducer 113. The switches 208, 209, 210 are controlled by the controller 202.

Depending on the design of a connected ultrasonic instrument, all or some of the inductances 205, 206, 207 are activated by the controller. A connected ultrasonic instrument is detected using known methods for instrument recognition, which do not need to be explained in more detail here. For example, information stored in the memory 130 of the ultrasonic instrument 10 can be evaluated.

The current and the voltage of the high-frequency electrical signal are sampled at short intervals via sensors 215, 216. From the sampled values, the controller 202 determines the phase position between current and voltage and controls the operating frequency of the oscillator 201 so that the current and voltage are in phase in order to energize the ultrasound transducer 113 at its resonant frequency.

If the oscillator 201 is now switched off to terminate the energizing of the ultrasonic instrument 10, the ultrasound transducer 113, the cable 10, and the connected inductances 205, 206, 207 form an electrical oscillating circuit that is excited by the energy stored in the system. Because the natural frequency of this oscillating circuit is not matched to the ultrasound transducer 113, current and/or voltage peaks can occur that can damage or destroy the ultrasound transducer 113.

Figure 5:
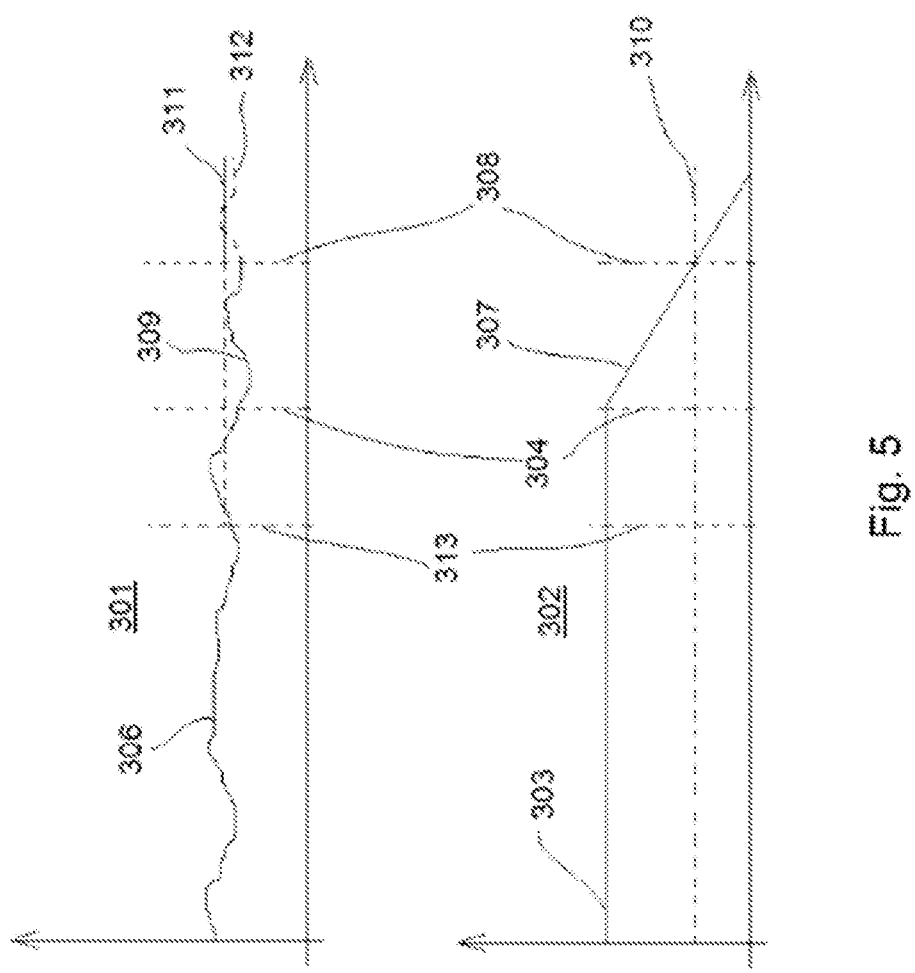

In order to prevent this, the operating amplitude of the ultrasound generator 20 is reduced in a controlled manner when the activation of the ultrasonic instrument 10 is ended; this is shown in FIG. 5. The upper diagram 301 shows the course of the operating frequency of the ultrasound generator over time, while the lower diagram 302 shows the course of the operating amplitude of the ultrasound generator over time.

The operating amplitude of the ultrasound generator 20 is initially constant (line 303) until the decay phase is initiated at a point in time 304, for example when a user of the electrosurgical system releases an activation switch, or when a predefined termination criterion for the treatment is reached. This can be, for example, a predefined treatment time or the reaching of certain electrical and/or mechanical impedance values or a predefined instrument or tissue temperature. Up to the point in time 304, the operating frequency of the ultrasound generator 20 is tracked with the resonant frequency of the ultrasound transducer 113 (line 306).

From the point in time 304, the output amplitude of the ultrasound generator 20 is changed, preferably reduced (line 307), at a predefined rate of change. While a linear reduction in the operating amplitude is shown in FIG. 5, this can also take place exponentially, in an S shape, or according to another time function.

Up to a point in time 308, the operating frequency of the ultrasound generator 20 is continuedly tracked with the resonant frequency of the ultrasound transducer 113 (line 309). At the point in time 308, the operating amplitude of the ultrasound generator 20 falls below a minimum operating amplitude (line 310) that is required to track the operating frequency with the resonant frequency. Therefore, from the point in time 308, the operating frequency of the ultrasound generator is kept at a fixed value (line 311), regardless of actual fluctuations in the resonant frequency (dashed line 312).

The value of the operating frequency of the ultrasound generator 20 after the point in time 308 is established on the basis of an average value that is determined, for example, between the point in time 313 that is before the point in time 304, and the point in time 304.

The point in time 313 can also be after the point in time 304 but before point in time 308, or it can correspond to the point in time 308.

The position of the point in time 308 at which the tracking of the operating frequency is ended can also be determined by a fixed time interval to the point in time 304 instead of falling below the minimum operating amplitude.

Although the invention has been described above on the basis of a forceps-like combined ultrasonic and high-frequency instrument 10, it can of course also be used in a purely ultrasonic instrument. The high-frequency generator 30 can be omitted here. The invention can also be used with other forms of instruments such as blades, spatulas or hooks.

It is also conceivable for the ultrasound generator 20 and the high-frequency generator 30 to be designed as a single device.

In addition to data for instrument recognition, other data can also be stored in the memory 130 of the ultrasonic instrument 10, which the ultrasound generator 20 uses in determining the resonant frequency. For example, a factory-determined resonant frequency can already be stored in the memory 130 and then read out by the ultrasound generator 20. Alternatively, a frequency range in which the resonant frequency is contained can also be stored in the memory 130 such that the ultrasound generator 20 can limit the scan process to this frequency range.

The invention claimed is:

1. A method for operating an electrosurgical system comprising an ultrasound generator and an ultrasonic instrument, comprising the steps:
   determining an initial resonant frequency of the ultrasonic instrument by means of the ultrasound generator,
   energizing the ultrasonic instrument by means of the ultrasound generator with an operating amplitude and an operating frequency which correspond to the initial resonant frequency, tracking the operating frequency of the ultrasound generator with changes in the resonant frequency of the ultrasonic instrument, and terminating the energizing of the ultrasonic instrument by the ultrasound generator, wherein, to terminate the energizing of the ultrasonic instrument by means of the ultrasound generator, in a decay phase the operating amplitude of the ultrasound generator is reduced to zero with a predefined or predefinable rate of change.

2. The method according to claim 1, wherein the operating frequency of the ultrasound generator is tracked with changes in the resonant frequency of the ultrasonic instrument at least in a first portion of the decay phase.

3. The method according to claim 2, wherein the transition between the first portion and the second portion of the decay phase takes place when the operating amplitude of the ultrasound generator falls below a predefined or predefinable limit value.

4. The method according to claim 2, wherein the transition between the first portion and the second portion of the decay phase takes place at a predefined or predefinable time after the initiation of the decay phase.

5. The method according to claim 1, wherein the operating frequency of the ultrasound generator is kept at a constant value at least in a second portion of the decay phase.

6. The method according to claim 5, wherein the operating frequency of the ultrasound generator is kept in the second portion of the decay phase at a value that corresponds to an average value of the operating frequency of the ultrasound generator in a predefined or predefinable time portion before the start of the second portion of the decay phase.

7. The method according to claim 6, wherein the predefined or predefinable time portion is completely before the start of the decay phase.

8. An ultrasound generator of an electrosurgical system comprising an ultrasound generator and an ultrasonic instrument, wherein the ultrasound generator is configured to operate the electrosurgical system according to a method according to claim 1.

* * * * *